US00PP26579P3

(12) United States Plant Patent
Morales

(10) Patent No.: US PP26,579 P3
(45) Date of Patent: Apr. 5, 2016

(54) ***ARBUTUS* PLANT NAMED 'MBAV13'**

(50) Latin Name: ***Arbutus* hybrid**
Varietal Denomination: MBAV13

(71) Applicant: Manuel Morales, Royal Oaks, CA (US)

(72) Inventor: Manuel Morales, Royal Oaks, CA (US)

( * ) Notice: Subject to any disclaimer, the term of this patent is extended or adjusted under 35 U.S.C. 154(b) by 307 days.

(21) Appl. No.: 13/986,998

(22) Filed: Jun. 21, 2013

(65) Prior Publication Data

US 2014/0380533 P1 Dec. 25, 2014

(51) Int. Cl.
*A01H 5/00* (2006.01)
*A01H 5/02* (2006.01)

(52) U.S. Cl.
USPC ..... Plt./226
CPC ..... *A01H 5/02* (2013.01)

(58) Field of Classification Search
USPC ..... Plt./226, 216
CPC ..... A01H 5/02; A01H 5/00
See application file for complete search history.

*Primary Examiner* — Kent L Bell
(74) *Attorney, Agent, or Firm* — Cassandra Bright

(57) ABSTRACT

A new and distinct *Arbutus* cultivar named 'MBAV13' is disclosed, characterized by variegated leaves and small growth form. The new variety is a *Arbutus*, typically produced as an outdoor ornamental plant.

3 Drawing Sheets

Latin name of the genus and species: *Arbutus* hybrid.
Variety denomination: 'MBAV13'.

BACKGROUND OF THE INVENTION

The new cultivar is the product of chance discovery. The new variety originated as a naturally occurring branch mutation of the unpatented 'Marina' variety of *Arbutus*. The new variety was discovered by the inventor, Manuel Morales, during the Fall of 2008 in a commercial nursery in Royal Oaks, Calif. After identifying the new variety as a potentially interesting selection, the inventor continued confidential testing and observation of 'MBAV13' to determine the stability of the interesting foliage variegation.

*Arbutus* 'Marina' is a well-known nursery tree, introduced commercially in 1984. While the variety is well-known, the actual species has not been determined. Horticultural industry members have proposed *Arbutus* 'Marina' to either be a selection of *Arbutus andrachnoides* or a hybrid between *Arbutus andrachnoides* and *Arbutus canariensis*. The inventor is unaware of the actual species.

Asexual reproduction of the new cultivar 'MBAV13' was first performed at a commercial nursery in Royal Oaks, Calif. by vegetative cuttings of the branch sport on a very limited basis beginning in late 2008. Access to all plants was restricted, as plants were kept in a location not open to the public. Through subsequent propagation, multiple generations have been reproduced, which have shown that the unique features of this cultivar are stable and reproduced true to type.

SUMMARY OF THE INVENTION

The cultivar 'MBAV13' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MBAV13'. These characteristics in combination distinguish 'MBAV13' as a new and distinct *Arbutus* cultivar:

1. Variegated foliage
2. Slow growth rate

PARENT COMPARISON

Plants of the new cultivar 'MBAV13' are similar to the parent, *Arbutus* 'Marina' in most horticultural characteristics. The new variety, however, produces variegated foliage, compared to the solid colored foliage of parent 'Marina'. Additionally, plants of 'MBAV13' are smaller and slower growing than plants of the parent variety[.]

COMMERCIAL COMPARISON

Plants of the new cultivar 'MBAV13' are best compared to the parent variety.

BRIEF DESCRIPTION OF THE PHOTOGRAPHS

The accompanying photograph in FIG. 1 illustrates in full color typical plants of 'MBAV13' grown in Royal Oaks, Calif. Plants are approximately 3 years old.

Figure 1:
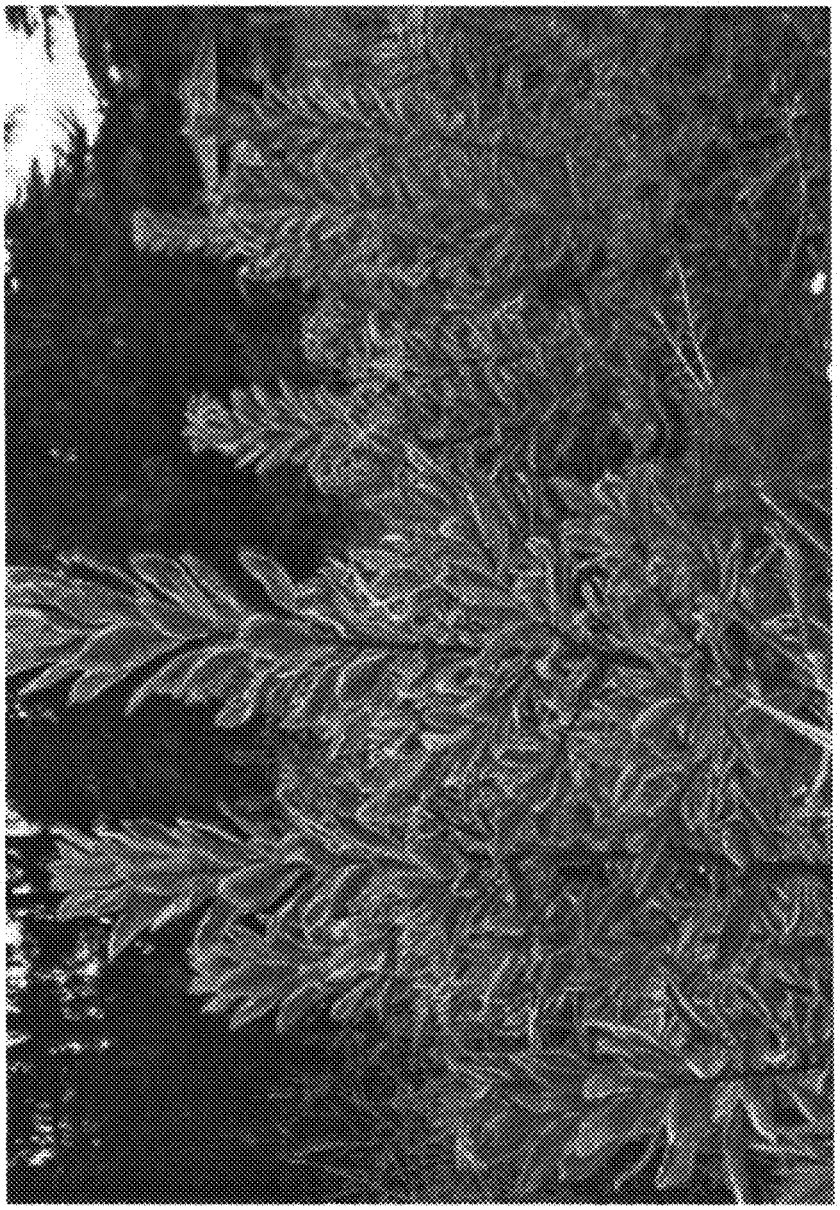
Figure 2:
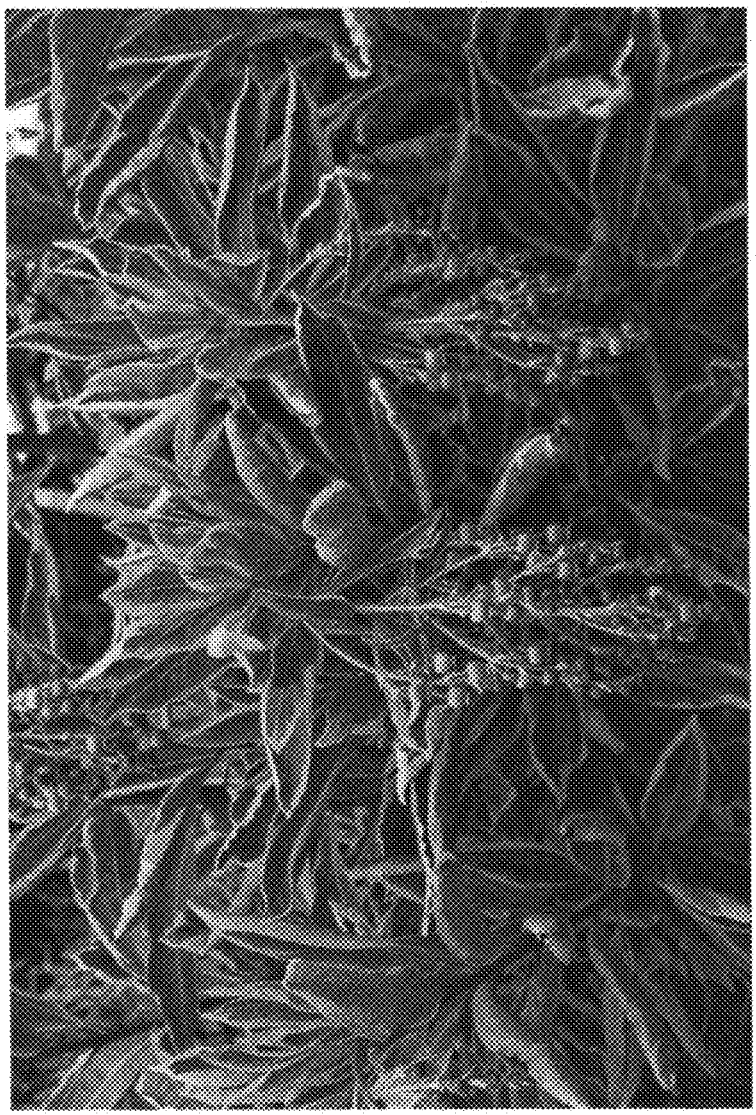
FIG. 2 illustrates in full color a close up of the flowers of 'MBAV13'.
Figure 3:
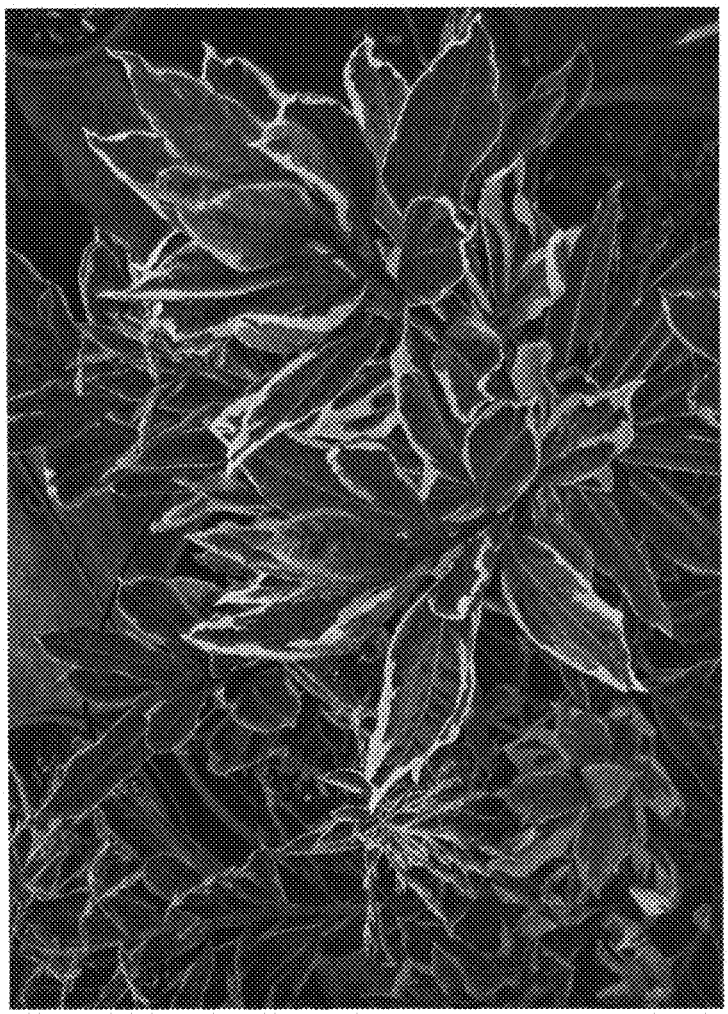
FIG. 3 illustrates young plants grown in liter pots.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'MBAV13' plants grown outdoors in Royal Oaks, Calif. Plants are approximately 1 year old. Temperatures ranged from approximately 1° C. to 15° C. at night and 10° C. to 32° C. during the day. No artificial light, photoperiodic treatments were given to the plants. No chemical treatments were given to plants. Measurements and numerical values represent averages of typical plant types.

Botanical classification: *Arbutus* 'MBAV13'.

PROPAGATION

Root description: Fine root system colored near Brown 199D and N199B.

PLANT

Growth habit: Small, often multi trunked tree.
Height: Approximately 30 cm for a one year old plant.
Plant spread: Approximately 20 cm.
Growth rate: Moderate, slower growth than non-variegated forms.
Diameter of stem: Approximately 0.7 cm.
Color of stem: Mature stems near RHS Brown 200B. Young growth near Greyed-Purple 187C.
Texture of stem: Scaly.

FOLIAGE

Leaf:
- *Arrangement*.—Opposite.
- *Quantity*.—Approximately 14 fully expanded leaves, and 6 smaller leaves per lateral branch.
- *Average Leaf length*.—Approximately 10 cm.
- *Average Leaf width*.—Approximately 3.5 cm.
- *Shape of blade*.—Elliptic.
- *Apex*.—Acute.
- *Base*.—Cuneate.
- *Margin*.—Shallow serrate.
- *Texture of top surface*.—Glabrous.
- *Texture of bottom surface*.—Glabrous.
- *Aspect*.—Somewhat undulating.
- *Color*.—Young foliage upper side: Near RHS Green 143B background color, thick margin Yellow-Green 154C, fine margin Red 53B. Young foliage under side: Near RHS Green 143B background color, thick margin Yellow-Green 154C. Mature foliage upper side: Near RHS Green 143B background color, thick margin Yellow-Green 154C, fine margin Red 53B. Mature foliage under side: Near RHS Green 143B background color, thick margin Yellow-Green 154C.
- *Venation*.—Type: Pinnate. Venation color upper side: Near RHS Yellow-Green 154C. Venation color under side: Near RHS Yellow-Green 154C.
- *Petiole*.—Length: Average 0.8 cm. Diameter: Approximately 0.2 cm. Color: Near RHS Yellow-Green 145C. Texture: Sparse, minute, stiff hairs.

FLOWER

Natural flowering season: Spring.
Length of flowering period: Approximately 8 weeks.
Inflorescence type: Mature, plants of at least 3 years old produce terminal clusters with approximately 40 individual, pendulous flowers per inflorescence. 1 year old plants produce inflorescence with approximately 10 to 20 flowers.
Individual flower type: Pendulous, urn shaped.
Bud:
- *Shape*.—Spherical.
- *Color*.—Near RHS Red 53C.
- *Diameter*.—Approximately 0.7 cm.
- *Height*.—Approximately 0.9 cm.

Inflorescence size, 1 year old plant:
- *Diameter*.—Approximately 6 cm.
- *Height*.—Approximately 10 cm.

Flower:
- *Length*.—Average 1.2 cm.
- *Width*.—Average 0.8 cm.
- *Shape*.—Urn shaped.

Petals:
- *Arrangement*.—Gamopetalous, fused into a single urn shaped floral unity. Individual petals indistinguishable.
- *Texture*.—Glabrous.
- *Apex*.—Crenate.
- *Base*.—Fused.
- *Margin*.—Entirely fused.
- *Color*.—When opening: Exterior surface: Near RHS Red-Purple 61B. Interior surface: Near RHS Red 55D. Fully opened: Exterior surface: Near RHS Red 55C at base, mid section near Red 55B, Apex near Red 56D. Interior surface: Near RHS Red 56B at base, mid section near Red 56A, Apex near Red 56D. Fading: Exterior surface: Near RHS Red 56C at base, mid section near Red 56B, Apex near Red 56D. Interior surface: Near RHS Red 56D.

Calyx/sepals:
- *Quantity per flower*.—5.
- *Shape*.—Narrow deltate.
- *Length*.—About 0.6 cm.
- *Width*.—About 0.3 cm.
- *Apex*.—Acute.
- *Base*.—Fused.
- *Margin*.—Entire.
- *Texture*.—Glabrous.
- *Color*.—Upper Surface: RHS Green 137 A. Lower Surface: RHS Green 138A.

Peduncle:
- *Length*.—Average range approximately 7.5 cm to 12 cm.
- *Diameter*.—Approximately 1 mm.
- *Color*.—Near RHS Greyed-Yellow 160D, flushed Greyed-Red 181D.
- *Texture*.—Pubescent.

Pedicel:
- *Length*.—25 mm.
- *Diameter*.—Approximately 1 mm.
- *Texture*.—Very slightly pubescent.
- *Color*.—Near RHS Red 54D.

Fragrance: None.

REPRODUCTIVE ORGANS

Stamens:
- *Number (per flower)*.—8 to 10.
- *Filament length*.—About 0.5 cm.

Anthers:

*Shape*.—Linear.

*Length*.—About 0.1 cm.

*Color*.—RHS Greyed-Yellow 160B.

Pollen:

*Color*.—RHS Greyed-Yellow 160A.

*Amount*.—Scant.

Pistils:

*Quantity per flower*.—1.

*Length*.—About 2.5 cm.

*Style*.—Length: about 0.8 cm. Color: RHS Green 137C. Stigma: Shape: Linear. Color: RHS Green 143C. Ovary Color: RHS Green 143A.

OTHER CHARACTERISTICS

Disease resistance: Neither resistance nor susceptibility to normal diseases and pests of *Arbutus* observed.

Temperature tolerance: Not tested but expected to handle a very slight frost, and high temperatures without humidity. Expected range from approximately −2° C. to 30° C.

Drought tolerance: Will tolerate some dryness once established.

Fruits:

*Type*.—Berry, fleshy with a slightly gritty texture.

*Height*.—Average 1.0 cm.

*Diameter*.—Average 1.0 cm.

*Shape*.—Sphere.

*Quantity*.—Typical clusters of 3 to 5. Also occurring singly, double or rarely up to 9 per cluster.

*Texture*.—Papillate.

*Skin color*.—Immature fruit Yellow-White near 158B, flushed Red 52C. Ripening fruit near Yellow 11B, heavily flushed Red 52C. Ripe fruit near Red 52B.

*Flesh color*.—Near RHS Greyed-Yellow 161C.

Fruit pedicel:

*Length*.—Average range 3 to 5 cm.

*Color*.—Near RHS Yellow-Green 145C.

*Texture*.—Glabrous.

Seeds: Infrequent and irregular production of seeds observed. If seeds present, 1 to 2 per chamber, typically 1 to 2 mm long, 1 mm wide, colored near Brown 200A.

What is claimed is:

1. A new and distinct cultivar of *Arbutus* plant named 'MBAV13' as herein illustrated and described.

* * * * *